United States Patent [19]
Connolly

[11] Patent Number: 5,171,694
[45] Date of Patent: Dec. 15, 1992

[54] METHOD FOR MONITORING AQUEOUS CARBON DIOXIDE

[75] Inventor: Dennis J. Connolly, Alliance, Ohio

[73] Assignee: The Babcock & Wilcox Company, New Orleans, La.

[21] Appl. No.: 730,188

[22] Filed: Jul. 12, 1991

Related U.S. Application Data

[62] Division of Ser. No. 499,142, Mar. 26, 1990, Pat. No. 5,068,090.

[51] Int. Cl.$^5$ .............................................. G01N 27/06
[52] U.S. Cl. ........................................ 436/134; 422/90; 422/82.02; 436/133; 436/150
[58] Field of Search .................. 422/90, 82.02; 436/68, 436/150, 133–134; 324/438–439, 450

[56] References Cited

U.S. PATENT DOCUMENTS

| | | | |
|---|---|---|---|
| 4,209,299 | 6/1980 | Carlson | 23/230 |
| 4,228,400 | 10/1980 | Bruckenstein | 324/450 |
| 4,293,522 | 10/1981 | Winkler | 422/80 |
| 4,517,135 | 5/1985 | Szerenyi et al. | 261/104 |

*Primary Examiner*—James C. Housel
*Assistant Examiner*—Lyle A. Alexander
*Attorney, Agent, or Firm*—Vytas R. Matas; Robert J. Edwards; Daniel S. Kalka

[57] ABSTRACT

An apparatus and method for the measurement of low levels of carbon dioxide in a sample employing membrane separation and ion-exchange technology. The difference in acid strength of carbonic acid and other acids is exploited by first treating the sample with a weak base in a membrane separator and then with a strong base in the membrane separator. In this manner, the carbonic acid is distinguished from the stronger acids. By converting carbonic acid to sodium carbonate, the conductivity level is enhanced facilitating more precise measurements.

3 Claims, 7 Drawing Sheets

METHOD FOR MONITORING AQUEOUS CARBON DIOXIDE

This is a division of application Ser. No. 07/499,142 filed Mar. 26, 1990 now U.S. Pat. No. 5,068,090.

BACKGROUND OF THE INVENTION

1. Field of the Invention

The present invention relates in general to the measurement of low levels of carbon dioxide dissolved in water, and in particular, is directed to a method and apparatus for measuring low levels of carbon dioxide dissolved in water employing membrane separation and trans-membrane ion exchange techniques.

2. Description of the Related Art

In monitoring power plant water chemistry, there are three electrical conductivity measurements of interest. These are specific conductivity, cation conductivity, and degassed cation conductivity.

The electrical conductivity or conductivity, which is a measure of the ionic content of a sample, is a non-specific measurement in that all of the ions in solution, both cations and anions, contribute to the total observed conductivity. Specific conductivity is the conductivity measurement obtained from an untreated sample. When the sample is passed through a cation exchange column, which exchanges all cations in solution for the most highly conductive cation, i.e., the hydrogen ion, the cation conductivity is then measured. After the sample passes through the cation exchange column, all of the anions are in their acid form. The degassed cation conductivity measurement is normally the third in this series of three conductivity measurements.

The degassed cation conductivity is a measure of the cation conductivity of a sample after all of the volatile substances which contribute to the conductivity are removed. Normally, the solution is heated to near the boiling point of water to expel carbon dioxide and the other volatile components. The conductivity of the sample is measured at the high temperature and one of several algorithms is used to relate the high temperature conductivity to the room temperature conductivity. Alternatively, the degassed sample can be cooled to room temperature before measuring the conductivity.

The current method for measuring low levels of carbon dioxide dissolved in water is the degassed cation conductivity method which is also known as the reboiler method. This method assumes that the main volatile constituent contributing to conductivity is the dissolved carbon dioxide which exists in solution as carbonic acid. In this way, the degassed cation conductivity when compared to cation conductivity is an indication of the carbon dioxide content of the sample. In power plants, these measurements allow for distinguishing conductivity increases due to cooling water leaks and air leakage.

There are several disadvantages to the degassed cation conductivity method. The first is that the method does not selectively remove carbon dioxide. At the high temperature, other volatile species are also driven off as well as the carbon dioxide. These include anions of interest like chloride and sulfate which have been converted to the more volatile hydrochloric acid and sulfuric acid by the cation exchange. A key premise of the degassed cation conductivity method is that these other anions are unaffected by the heating process.

Another disadvantage is that the method is probably incomplete. An air saturated water sample contains approximately 0.5 to 1 ppm of total carbonate depending on temperature and pressure from the carbon dioxide in the air. In solution, carbon dioxide is distributed among several forms including carbonate ($CO_3$), bicarbonate ($HCO_3$), carbonic acid ($H_2CO_3$), and carbon dioxide in various forms of hydration. The volatile forms are the non-ionic species. At a pH of 5.7, which is a typical value for air saturated water, the non-volatile carbonate and bicarbonate constitute about 20% of the total carbonate content. Thus, at any one time, only 80% is available for removal due to volatility. Under static conditions, as carbon dioxide is removed, the 20% non-volatile portion is shifted toward the volatile forms and 100% removal is theoretically achievable. However, this method is a flowing system. Slowing the flow to aid in efficiency of carbon dioxide removal also increases the opportunity to boil off other anions leading to an erroneous result.

Still another disadvantage is that useful results require the determination of small differences in conductivity. For example, in a solution which is a 300 ppb chloride (as HCl) and 500 ppb carbonate, the theoretical conductivity is 3.764 microsiemens per centimeter ($\mu S/cm$). If all the carbonate is removed, the conductivity due to 300 ppb chloride is 3.607 $\mu S/cm$). Thus, the carbon dioxide content of the sample is measurable by a difference of only 0.157 $\mu S/cm$.

A further disadvantage of the degassed cation conductivity method is that a practical interpretation of the conductivity measured at the outlet relies on a mathematical relationship between the conductivity at 98° C. and the corresponding room temperature conductivity. The alternative method of cooling the sample back to room temperature before measurement introduces the possibility of readmitting carbon dioxide to the sample through air ingress. Additionally, the high temperature process may result in corrosion, the conductive products of which will give erroneously high conductivity measurements.

Thus there is a need for an apparatus and method which measures low levels of carbon dioxide dissolved in water without the disadvantages of the degassed cation conductivity method. A method is needed where conductivity measurements are taken at an ambient temperature to eliminate reliance on mathematical algorithms for conversion of data and which eliminates concern from potentially interfering high temperature reactions. There is a need for higher precision in the interpretation of measured data to provide confidence and useful results in measuring carbon dioxide content of the sample by increasing the conductivity measurements.

While it is known in ion chromatography how to suppress high background conductivity with membrane based cation exchange systems for greater sensitivity, heretofore there are no methods available with trans-membrane ion exchange techniques that allow for the measurement of low levels of carbon dioxide in water.

SUMMARY OF THE INVENTION

The present invention solves the aforementioned problems by providing a method and apparatus for measuring low levels of carbon dioxide dissolved in water. The present invention utilizes membrane separation and trans-membrane ion exchange techniques to exploit the difference in acid strength between carbonic acid (aqueous carbon dioxide) and other acids typically found in cation exchange effluent.

Accordingly, the present invention provides a method and apparatus for measuring low levels of carbon dioxide dissolved in water.

In a first embodiment, the sample is passed through cation exchange resin. This effluent is treated with first a weak base (for example, sodium sulfate) for producing a first solution of which the conductivity is measured. The first solution contains the sodium salts of strong acids with carbonic acid being substantially unreacted. This first reaction occurs in a membrane separator which keeps the reactants separate while allowing cations to exchange.

A valve means then allows a strong base (for example, sodium hydroxide) to pass through the membrane separator to convert the carbonic acid in the first solution to sodium carbonate. The conductivity of this second solution is measured. The carbon dioxide concentration is determined from the change in conductivity.

In the preferred embodiment, a sample representing the cation exchange column effluent is passed through a first membrane separator where it is treated with a weak base. The solution exiting the first membrane separator consists of the sodium salts of the strong acids but the remaining carbonic acid is unaffected. Prior to entering the first membrane separator, the conductivity of the sample may be measured. The solution exiting the first membrane separator has its conductivity measured. Next, the sample enters a second membrane separator where it is treated with a strong base to convert the carbonic acid to sodium carbonate. The conductivity is then measured as the second solution exits the second membrane separator. The change in conductivity that results from the solution exiting the first membrane separator and the second solution exiting the second membrane separator represents the carbonate concentration of the sample. The conductivities of carbonic acid and sodium carbonate are plotted as conductivity versus concentration curves for the range of interest. From the carbonate concentration the carbon dioxide concentration is obtained with a mathematical ratio.

An aspect of the present invention is to provide an apparatus and method for measuring low levels of carbon dioxide dissolved in water based on a combination of membrane separation and ion exchange processes.

Yet another aspect of the present invention is to obtain higher precision in the interpretation of measured data by amplifying the measured parameter from less conductive to more conductive forms.

Still another aspect of the present invention is to take conductivity measurements at ambient temperature to eliminate the reliance on mathematical algorithms for the conversion of high temperature data.

The various features of novelty characterized in the present invention are pointed out with particularity in the claims annexed to and forming a part of this disclosure. For a better understanding of the invention, the operating advantages gained by its use, reference is made to the accompanying drawings and descriptive matter in which a preferred embodiment of the present invention is illustrated.

DESCRIPTION OF THE PREFERRED EMBODIMENT

Figure 1:
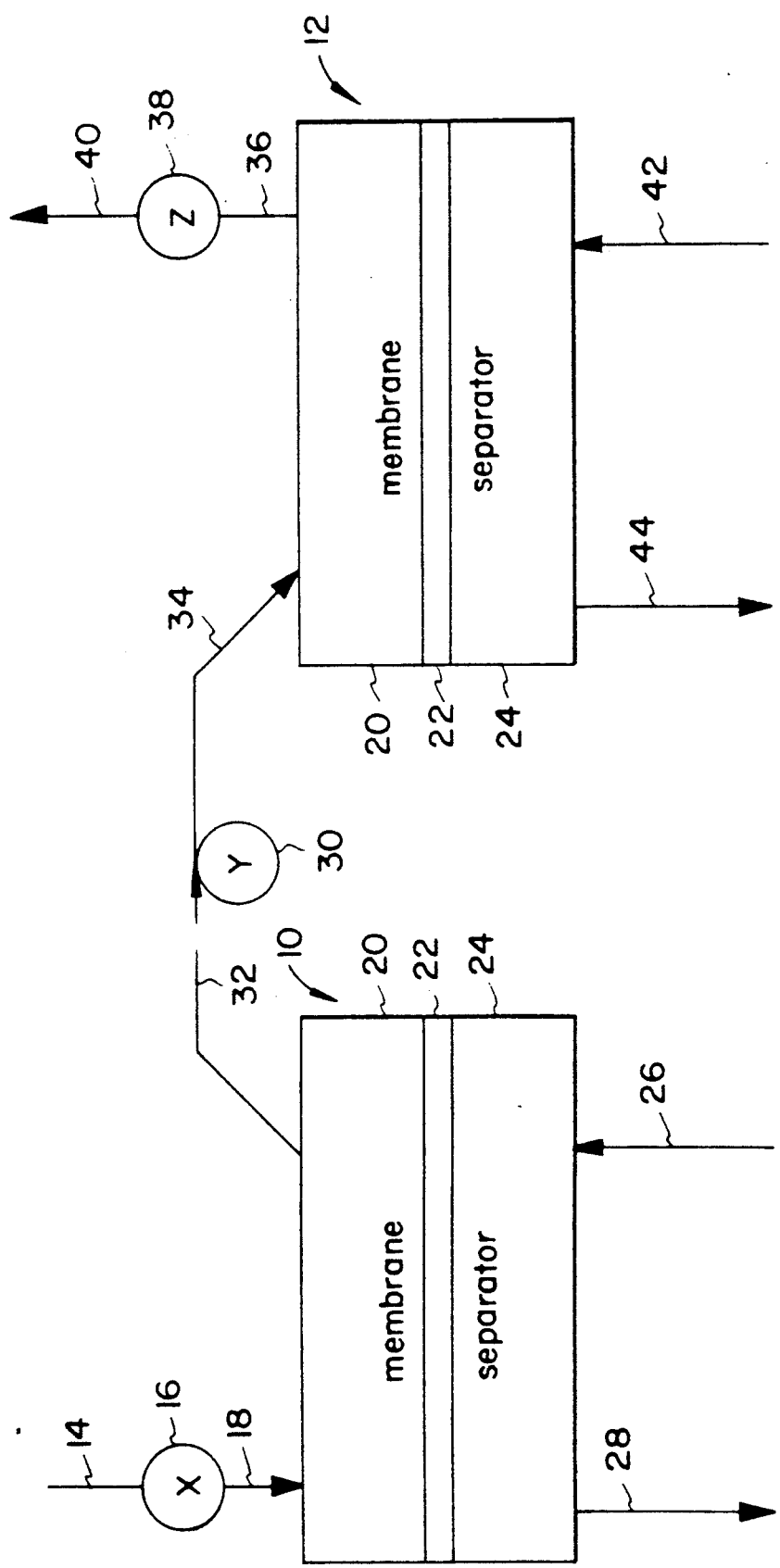
FIG. 1 is a schematic illustration of the preferred system operating in accordance with the present invention.

The present invention resides in a method and apparatus for the measurement of low levels of carbon dioxide dissolved in a sample such as a water. It is based on a combination of membrane separation and ion exchange processes. The present invention exploits the difference in acid strength between carbonic acid, i.e., aqueous carbon dioxide, and other acids typically found in cation exchange effluent.

Chemically, carbonic acid differs from other acids in a typical cation exchange effluent in that it is only partially ionized. It is referred to as a weak acid as compared to acids like hydrochloric or sulfuric which are totally ionized in water. This is the reason that the contribution of carbonic acid to the total conductivity is relatively minor so that even if carbonic acid could be selectively and completely removed, the resulting change in conductivity is small. This difference in acid strength is exploited in that neutralization reactions selectively discriminate between the strong and the weak acids through the use of different base strengths as neutralizing agents. The following equation represents the reaction between a weak acid and a weak base:

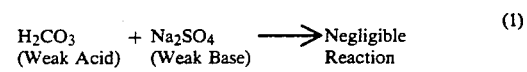

$$H_2CO_3 + Na_2SO_4 \longrightarrow \text{Negligible Reaction} \quad (1)$$
(Weak Acid) (Weak Base)

The extent to which reaction 1 takes place depends on both the acid and the base strength and the concentrations of the reactants. With the selection of a weak base strength and concentration, the reaction proceeds to only a negligible extent.

The reaction of a strong acid and a weak base is depicted in the following manner:

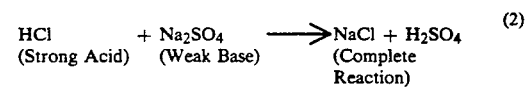

$$HCl + Na_2SO_4 \longrightarrow NaCl + H_2SO_4 \quad (2)$$
(Strong Acid) (Weak Base) (Complete Reaction)

A combination of the first and the second reactions is illustrated with a solution consisting of a strong acid, a weak acid, and a weak base. The strong acid is completely neutralized by being converted to its sodium salt while the weak acid remains unaffected as follows:

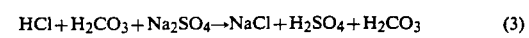

$$HCl + H_2CO_3 + Na_2SO_4 \rightarrow NaCl + H_2SO_4 + H_2CO_3 \quad (3)$$

Both a strong acid and a weak acid are neutralized with the addition of a strong base, such as sodium hydroxide, in the following way:

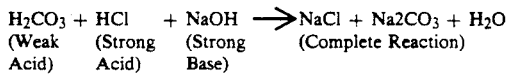

$H_2CO_3$ + HCl + NaOH → NaCl + $Na_2CO_3$ + $H_2O$
(Weak Acid) (Strong Acid) (Strong Base) (Complete Reaction)

The present invention exploits the difference in acid strengths illustrated in the above neutralization reactions to selectively discriminate between the strong and weak acids through the use of different base strengths as neutralizing agents.

For the above reactions to be useful to the present invention, it is desirable to keep the reactants separate but allow only the exchange reaction, that is the hydrogen ions for sodium ions to take place. In this way, the conductivity of the acids as sodium salts may be measured without interference from the bases and their counter ions.

The term "strong base" is defined as a base which completely dissociates in water. An example of a strong base is sodium hydroxide. A "weak base" only partially dissociates and the degree of dissociation is defined by a dissociation constant, Kb, as follows:

$$Base \cdot OH \rightleftharpoons Base^+ + OH^-$$

$$Kb = \frac{[Base^+][OH^-]}{[Base \cdot OH]}$$

The degree of neutralization between a hypothetical acid, HA, and a hypothetical base, BOH, depends on both the acid and base strengths as follows:

$$HA + BOH \rightleftharpoons H_2O + AB$$

The equilibrium constant, K, for this neutralization reaction is a function of the acid dissociation constant, Ka, the base dissociation constant, Kb, and the water dissociation constant, Kw, as follows:

$$K = \frac{KaKb}{Kw}$$

Thus, the degree of neutralization may be controlled by choosing acids and bases of particular strength depending on the extent of neutralization which is desired.

Figure 6:
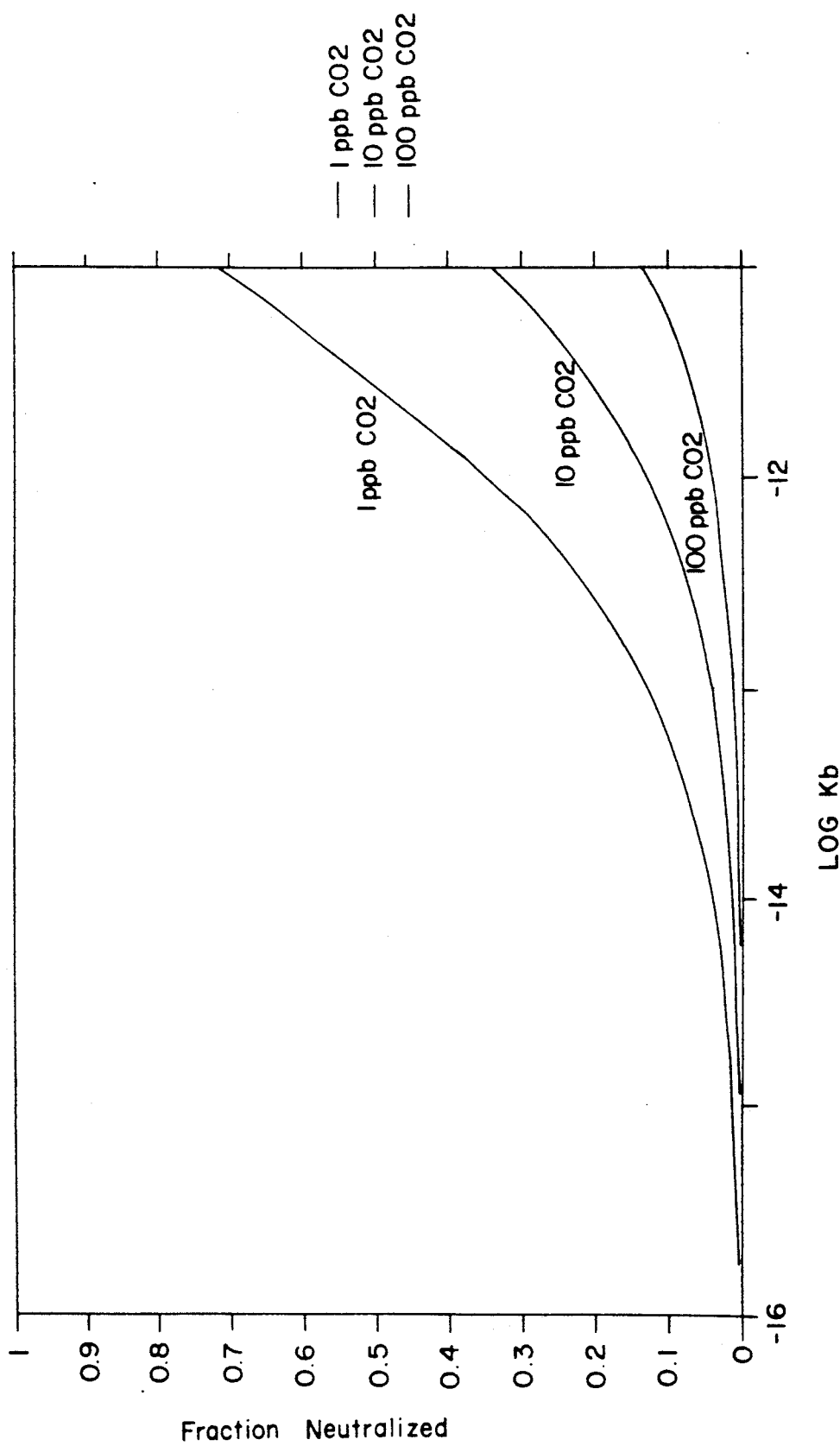
FIG. 6 is a graph showing how a particular base strength may be selected to achieve a desired low degree of neutralization.
Figure 7:
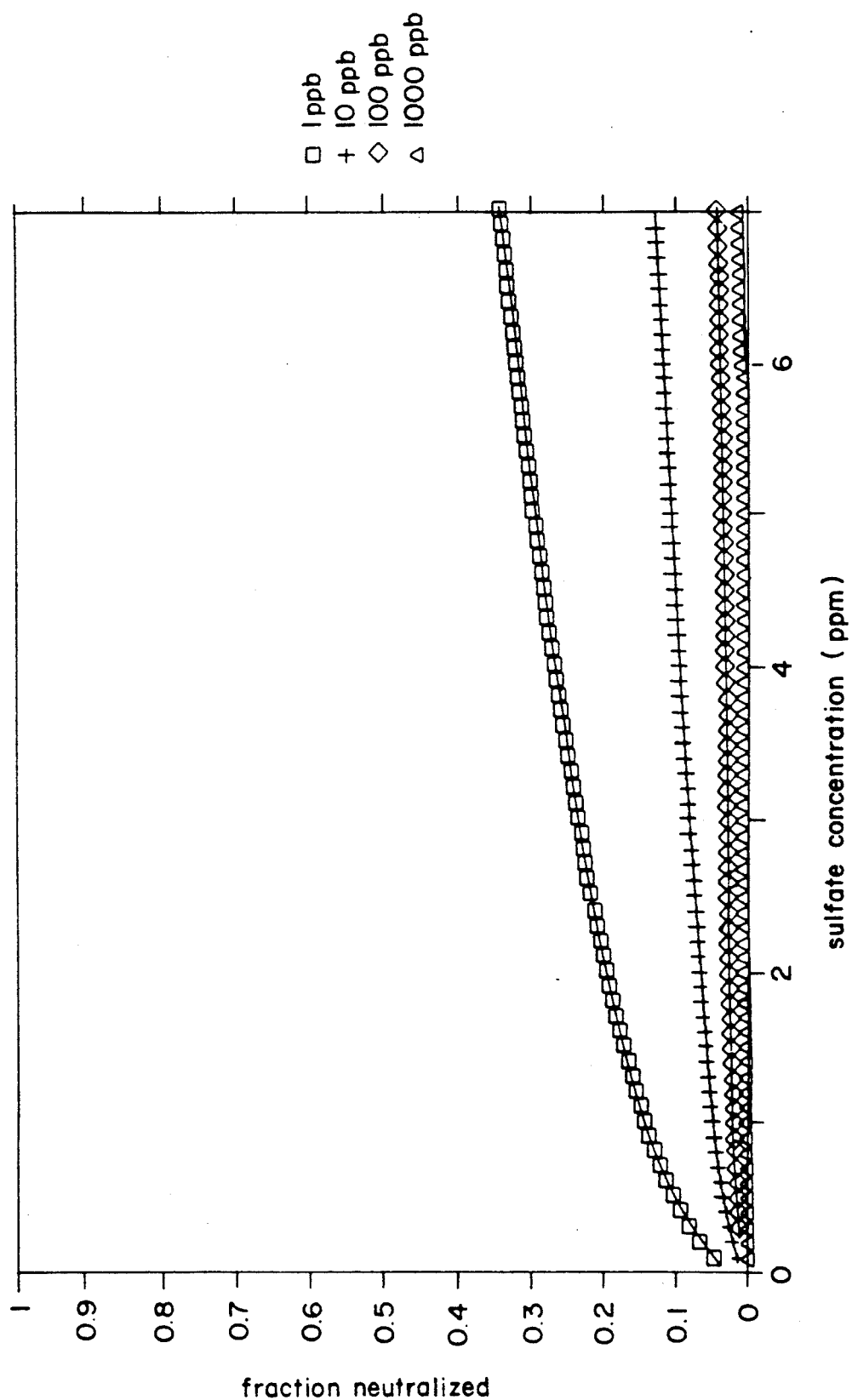
FIG. 7 is a graph showing how the degree of neutralization of carbonic acid using sodium sulfate may be kept to a specified low value.

For carbonic acid in a cation exchange effluent to remain substantially unreacted (un-neutralized), a base is chosen whose strength (dissociation constant) will keep the neutralization equilibrium value to a low or negligible value. FIG. 6 shows how a particular base strength may be selected to achieve a desired low degree of neutralization. FIG. 7 shows how the degree of neutralization of carbonic acid using sodium sulfate may be kept to a specified low value.

In the preferred embodiment depicted in FIG. 1, there is a first membrane separator 10 and a second membrane separator 12. Both membrane separators 10, 12 have two compartments 20, 24 separated by a membrane 22 which allows for the exchange of ions. The sample stream flows from a cation exchange column (not shown) along line 14 through a first conductivity cell 16 which measures the sample conductivity. This is the traditional cation conductivity. The sample proceeds along line 18 to the first compartment 20 of the first membrane separator 10. Within the first membrane separator 10, a weak base (sodium sulfate) flows counter to the flow of the sample on the opposite side of the membrane 22 in the second compartment 24 of the first membrane separator 10. The weak base enters the first membrane separator 10 by way of line 26 and exits via line 28. In the first membrane separator 10, membrane 22 allows sodium ions to be exchanged for hydrogen ions. The reaction illustrated in Reaction 3 occurs and the acid formed from the reaction exits via line 28 while the first solution exiting the first compartment 20 consists of the sodium salts of the strong acids but the carbonic acid in the sample is unaffected.

As the solution exits the first membrane separator 10 via line 32, a second conductivity cell 30 allows the conductivity of the first solution to be measured.

The first solution flows into the second membrane separator 12 by way of line 34 where a strong base such as sodium hydroxide flows in a similar fashion as the weak base in the first membrane separator 10. This treatment converts all of the carbonic acid to sodium carbonate. This second solution moves via line 36 to conductivity cell 38 for conductivity measurement and exits by way of line 40.

The change in conductivity measured at conductivity cells 30 and 38 is described as follows:

$\Delta C = C(Z) - C(Y) =$
C(strong acid salts + $Na_2CO_3$) −
C(strong acid salts + $H_2CO_3$)

where:

C(Z) = the conductivity measurement at conductivity cell 38;

C(Y) = conductivity measurement at conductivity cell 30;

Then, since the strong acid salt concentration is constant between cell 30 and cell 38, it follows that:

$\Delta C = C(Na_2CO_3) - C(H_2CO_3)$

Figure 2:
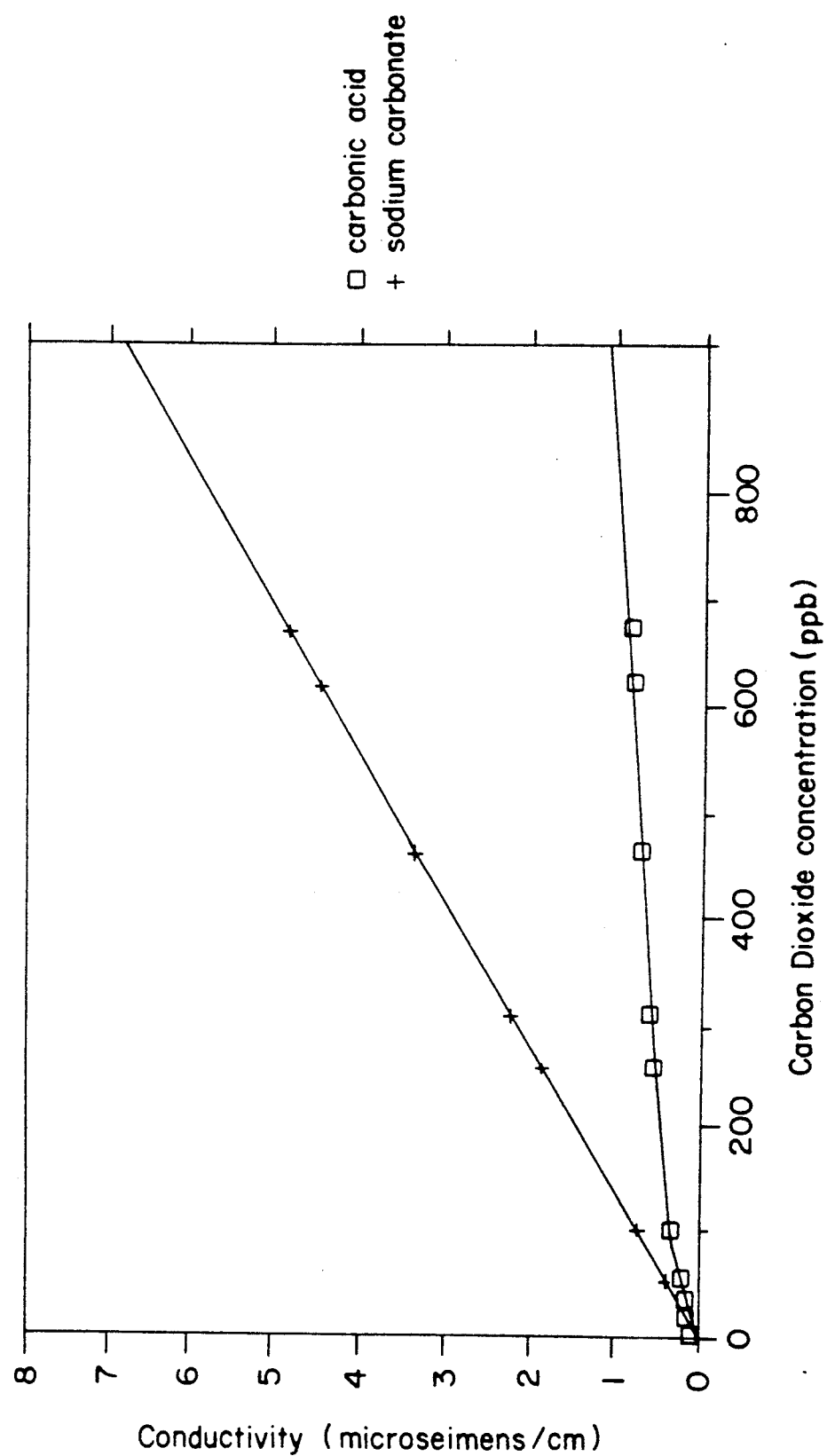
FIG. 2 is a graph showing the conductivity of carbonic acid and the conductivity of sodium carbonate as a function of total carbon dioxide concentration.
Figure 3:
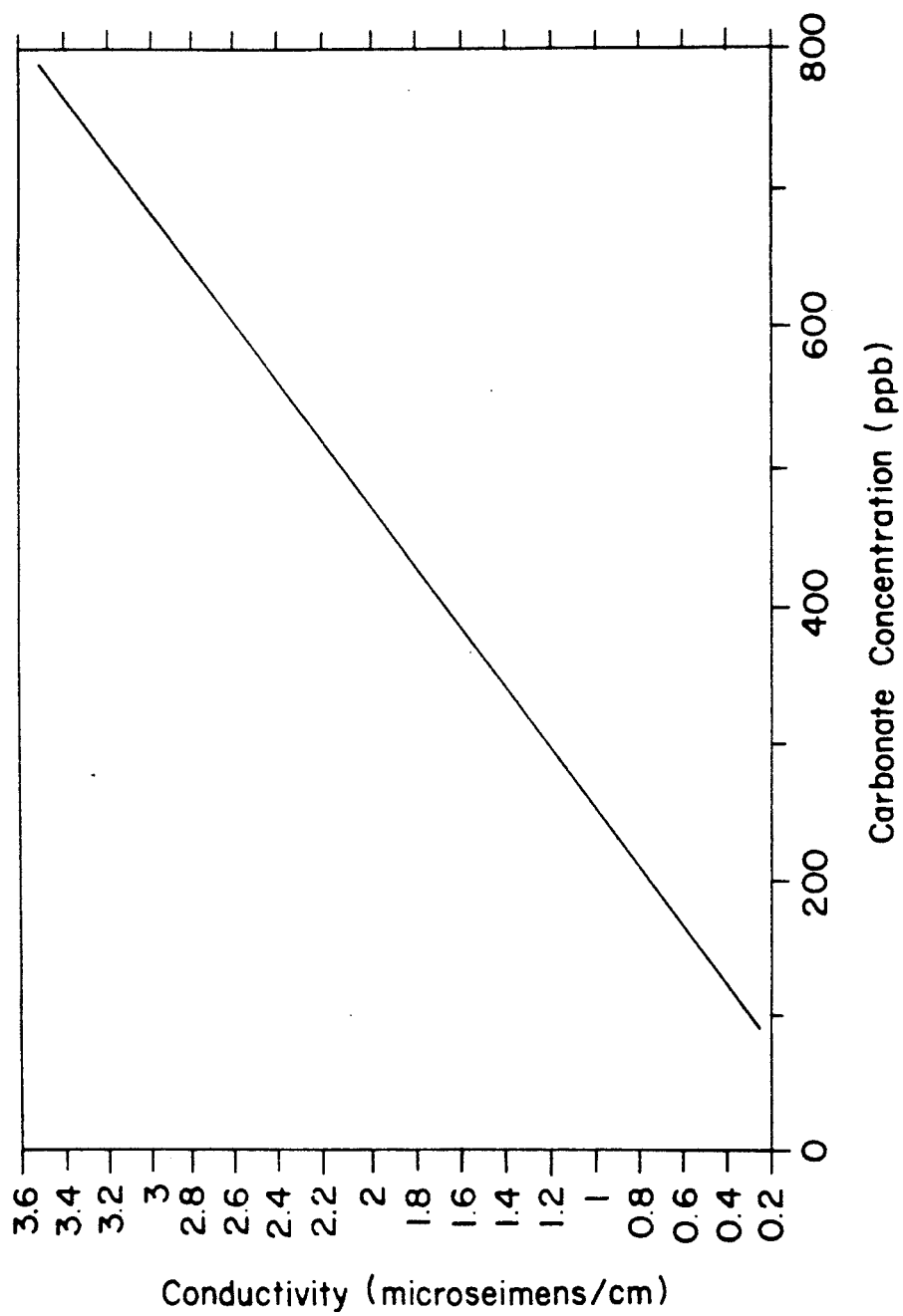
FIG. 3 is a graph showing the conductivity difference between sodium carbonate and carbonic acid solutions as a function of carbonate concentration.

The carbonate concentration of the sample is determined from this conductivity difference. The conductivity of carbonic acid and the conductivity of sodium carbonate are shown in FIG. 2 as a function of total carbon dioxide concentration. The difference between these two curves covering the range of about 100–750 ppb carbonate is shown in FIG. 3. This curve is approximately linear with a slope of 209.0. The carbonate concentration is determined by multiplying the measured conductivity difference by 209.0. From the carbonate concentration, as determined from FIG. 3, the carbon dioxide concentration in terms of $CO_2$ is obtained by multiplying by the ratio of the respective molecular weights in the following manner:

$$[CO_2] = \frac{44}{60}[CO_3]$$

Of course, it is to be understood that the curves illustrated in FIGS. 2 and 3 may be mathematically defined so as to enable the direct readout of carbon dioxide content with a suitable microprocessor or computer (not shown).

With reference back to FIG. 1, if specific conductivity of the sample stream is desired, then a conductivity cell should be positioned prior to the cation exchange column so as to measure the conductivity of the untreated sample.

EXAMPLE I

Figure 5:
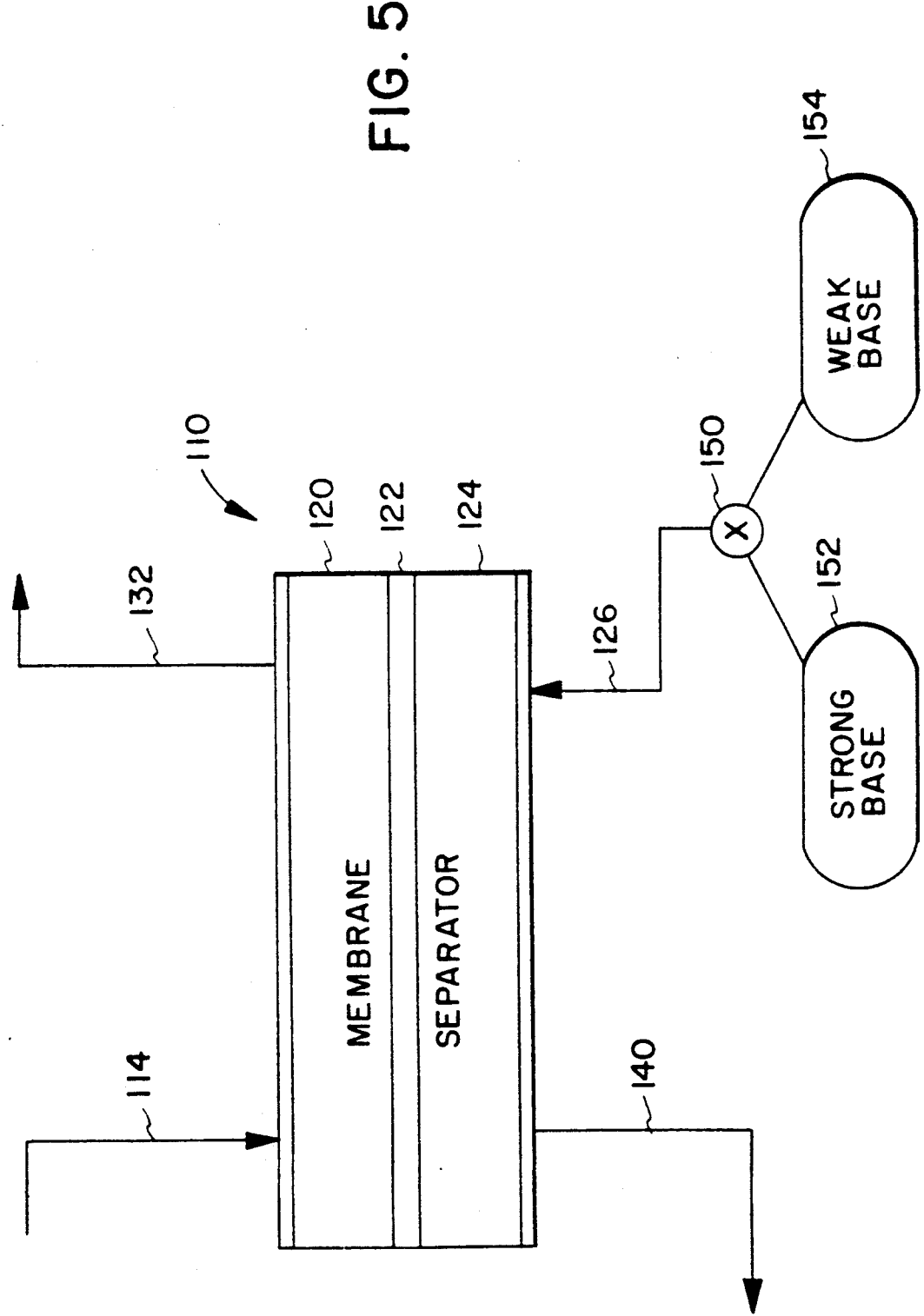
FIG. 5 is a schematic depiction of another embodiment of the present invention.

The concept of the present invention was demonstrated on the embodiment depicted in FIG. 5. In FIG. 5, the sample solution is pumped through a single membrane separator 110. The membrane separator 110 consists of a first compartment 120 separated by a membrane 122 from a second compartment 124. Valve switching means 150 provides for different reagents to promote the different exchange reactions from the weak base 154 and the strong base 152. The conductivity before and after the membrane separator 110 is measured with a conductivity cell (not shown). This embodiment is operated in accordance with the description of the preferred embodiment shown in FIG. 1.

A sample pump causes the sample stream and reagents to flow through membrane separator 110. A Bowdine Electric Company fractional horse power gearmotor was used. The conductivity cells were manufactured by Beckman Instruments. The conductivities were measured with a Leads and Northrup electrolytic conductivity bridge. The membrane separator 110 employed was a Dionex Anion Micro Membrane Suppressor (AMMS). The reagent bases 154, 152 were stored in five liter plastic carboys which were pressurized with nitrogen to provide flow through the membrane separator 110.

The sample solution consisted of a high purity, demineralized water which was air saturated to provide the weak acid content (aqueous carbon dioxide) and to which varying amounts of hydrochloric acid were added to provide the strong acid content.

The reagent bases used were 28 ppm ($1.97 \times 10^{-4}$M) sodium sulfate (weak base) 154 and 412 ppm ($1.04 \times 10^{-3}$M) sodium hydroxide (strong base) 152. The membrane separator 110 was operated in accordance with the guidelines provided by the manufacturer. According to these guidelines, the dynamic concentration, i.e., molarity x flow, the reagent should be at least five times that of the species in the test solution for which an exchange reaction is to be effected. The flow rates of both the test solution and the reagent bases were approximately 1.0 ml/min. The base strengths used were chosen so that their dynamic concentrations would be at least five times that of the anticipated acid content of the test solution. For field operation, depending upon the expected content of the sample water, the base concentrations may be adjusted.

RESULTS

The results of several test runs using this method of carbon dioxide determination are listed. Influent conductivity refers to the conductivity of the test solution prior to any exchange reaction with reagent bases. Effluent conductivity refers to the conductivity of the solution following the exchange reaction with the indicated base. $\Delta C$ is the difference in conductivity between the sodium sulfate (weak base) reaction effluent and the sodium hydroxide (strong base) reaction effluent. The carbon dioxide concentration is given as the product, $\Delta C \times 209.0$. Theoretical conductivities were calculated from known concentrations and the equivalent conductivities of the relevant chemical species.

| Influent Conductivity | | | Effluent Conductivity | |
|---|---|---|---|---|
| Measured | Theoretical | Treatment | Measured | Theoretical |
| Test 1 Test Solution: Aerated High Purity Water | | | | |
| 1.12 | .055 + $CO_2$ | None | 1.12 | .055 + $CO_2$ |
| 1.12 | .055 + $CO_2$ | $Na_2SO_4$ | 1.12 | .055 + $CO_2$ |
| 1.12 | .055 + $CO_2$ | NaOH | 3.24 | .055 + $\Delta C$ |
| | | $\Delta C = 2.12$ | | |
| | | $[CO_3] = \Delta C \times 209.0 = 442.6$ ppb | | |
| Test 2 Test Solution: 244 ppb chloride as HCl in High Purity Aerated Water | | | | |
| 3.10 | 2.934 + $CO_2$ | None | 3.08 | 2.934 + $CO_2$ |
| 3.10 | 2.934 + $CO_2$ | NaOH | 4.02 | 0.926 + $\Delta C$ |
| 3.09 | 2.934 + $CO_2$ | $Na_2SO_4$ | 1.48 | 0.926 + $CO_2$ |
| 3.01 | 2.934 + $CO_2$ | NaOH | 4.02 | 0.926 + $\Delta C$ |
| | | $\Delta C = 2.54$ | | |
| | | $[CO_3] = \Delta C \times 209.0 = 530.3$ ppb | | |
| Test 3 Test Solution: 125 ppb chloride as HCl in High Purity Aerated Water | | | | |
| 1.88 | 1.504 + $CO_2$ | NaOH | 4.40 | 0.501 + $\Delta C$ |
| 1.88 | 1.504 + $CO_2$ | $Na_2SO_4$ | 1.20 | 0.501 + $CO_2$ |
| 1.85 | 1.504 + $CO_2$ | NaOH | 4.51 | 0.501 + $\Delta C$ |
| | | average NaOH treated conductivity = 4.46 | | |
| | | $\Delta C = 3.26$ | | |
| | | $[CO_3] = \Delta C \times 209.0 = 679.5$ | | |
| Test 4 Test Solution: 1.04 ppm chloride as HCl in High Purity Aerated Water | | | | |
| 12.60 | 12.502 + $CO_2$ | NaOH | 7.19 | 3.772 + $\Delta C$ |
| 12.60 | 12.502 + $CO_2$ | $Na_2SO_4$ | 4.20 | 3.772 + $CO_2$ |
| | | $\Delta C = 2.99$ | | |
| | | $[CO_3] = \Delta C \times 209.0 = 624.2$ | | |
| Test 5 Test Solution: 520 ppb chloride as HCl in High Purity Aerated Water | | | | |
| 5.89 | 6.251 + $CO_2$ | $Na_2SO_4$ | 2.82 | 1.911 + $CO_2$ |
| 5.90 | 6.251 + $CO_2$ | NaOH | 5.20 | 1.911 ± $\Delta C$ |
| | | $\Delta C = 2.38$ | | |
| | | $[CO_3] = \Delta C \times 209.0 = 496.9$ | | |

The present invention provides several advantages over the currently employed degassed cation conductivity method. The first advantage is that the present invention is selective for weak acids since the method is based on thermodynamic considerations of acid-base relationships. Unfortunately, the present invention lacks the ability to distinguish between carbonic acid and other coexisting weak acids like acidic and/or formic acid. However, it is believed that by selection of appropriate reagent base strengths and dynamic concentration through the membrane/ion exchange separator, distinction among these acids may be feasible.

Figure 4:
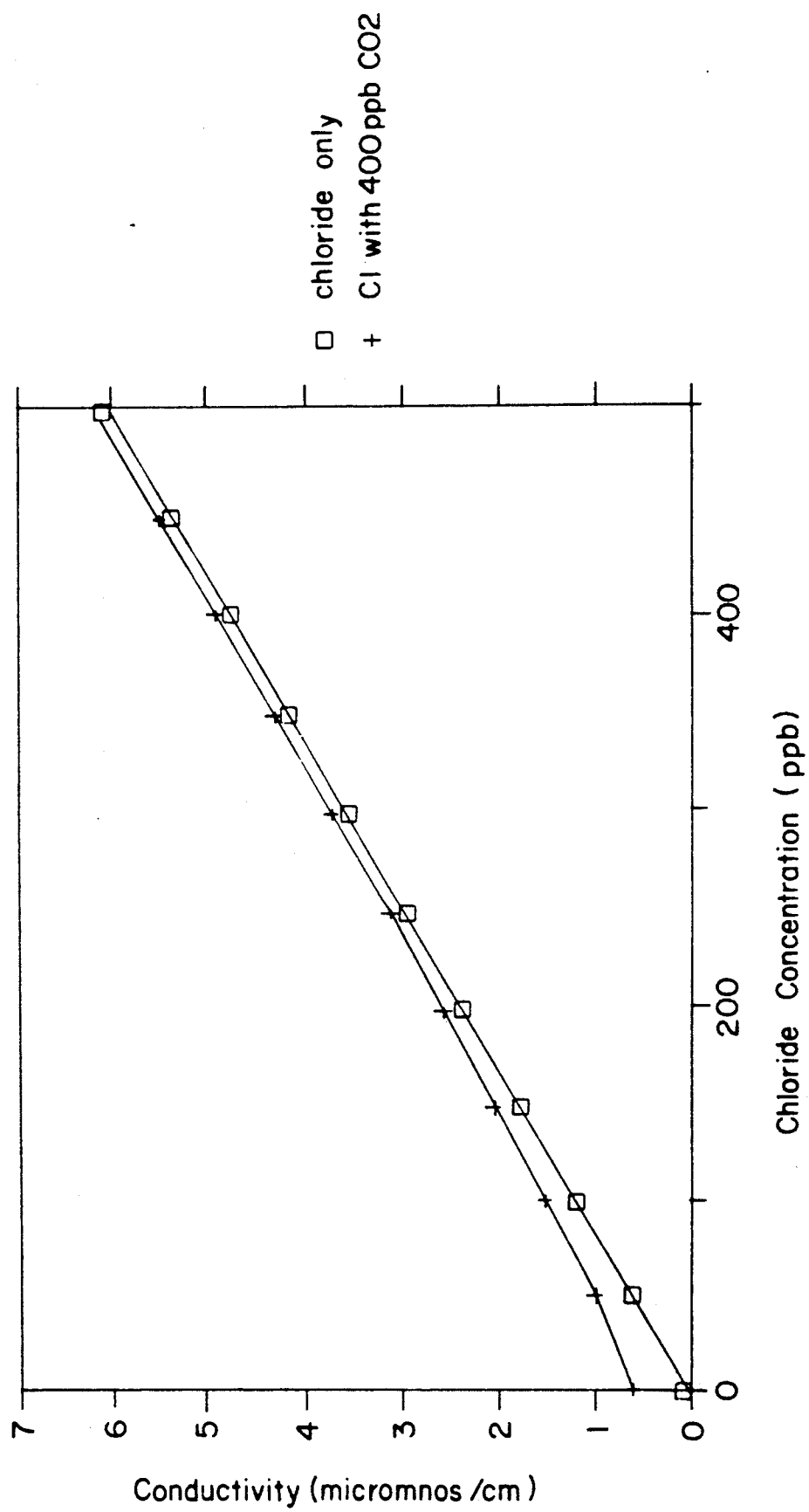
FIG. 4 is a graph depicting the differences in chloride and carbonate conductivity.

Another advantage of the present invention is higher precision in the interpretation of measured data obtained since the measured parameter, $\Delta C$, is amplified by conversion from less conductive to more conductive forms of the analyte (carbonic acid). This advantage is demonstrated by referring to FIG. 4. FIG. 4 shows the conductivity difference between various levels of chloride ion alone and the same levels of chloride in the presence of 400 ppb/$CO_2$ (as carbonate). This difference is a parameter measured with the degassed cation conductivity method. By comparison, FIG. 2 illustrates the much larger $\Delta C$ parameter measured with the present invention.

Still another advantage of the present invention is that conductivity measurements are taken at ambient temperature which eliminates reliance on mathematical algorithms for the conversion of high temperature data. Additionally, there is no concern from potentially interfering high temperature reactions.

The foregoing example is intended for illustrative purposes and is not meant to limit the present invention only to this application.

While a specific embodiment of the invention has been shown and described in detail to illustrate the principles of the present invention, certain modifications and improvements will occur to those skilled in the art upon reading the foregoing description. It is thus understood that all such modifications and improvements have been deleted herein for the sake of conciseness and readability but are properly in the scope of the following claims.

One example of such a modification would be to include a valve switching means connected to a solvent system for cleaning the apparatus after an analysis.

I claim:

1. A method for measuring low levels of carbon dioxide in a water sample comprising the steps of:

passing a sample through a cation exchange resin;

passing the sample through a first membrane separator where said first membrane separator has a first compartment for receiving the sample and second compartment separated by a membrane that allows for an exchange of ions between the compartments, said second compartment supplies a weak base which ions cross the membrane to neutralize any strong acid in the sample in the first compartment and will leave unreacted carbonic acid in the sample;

taking a first conductivity measurement of the sample exiting from the first compartment of the first membrane separator;

passing said sample from the first compartment of the first membrane separator to a second membrane separator where said second membrane separator has a first compartment for receiving the sample and a second compartment separated by a membrane that allows for an exchange of ions between the compartments, said second compartment supplies a strong base which ions cross the membrane to convert the carbonic acid in the sample stream to a carbonate salt; taking a second conductivity measurement of the sample exiting from the first compartment of the second membrane separator;

comparing the first and second conductivity measurements for a change in the conductivity; and determining the carbon dioxide content of the sample from any change in conductivity.

2. A method as recited in claim 1, further comprising the step of measuring conductivity of the sample after it has passed through the cation exchange resin to provide a cation conductivity measurement for the sample.

3. A method as recited in claim 2, further comprising the step of measuring conductivity of the sample prior to passing it through the cation exchange resin to provide a specific conductivity measurement for an untreated sample.

* * * * *